United States Patent
Brendel et al.

(10) Patent No.: US 10,052,078 B2
(45) Date of Patent: Aug. 21, 2018

(54) SEGMENTATION OF MOVING STRUCTURE IN IMAGE DATA

(71) Applicant: KONINKLIJKE PHILIPS N.V., Eindhoven (NL)

(72) Inventors: Bernhard Johannes Brendel, Norderstedt (DE); Michael Grass, Buchholz in der Nordheide (DE); Holger Schmitt, Luetjensee (DE); Sven Kabus, Hamburg (DE)

(73) Assignee: KONINKLIJKE PHILIPS N.V., Eindhoven (NL)

(*) Notice: Subject to any disclaimer, the term of this patent is extended or adjusted under 35 U.S.C. 154(b) by 61 days.

(21) Appl. No.: 15/112,439

(22) PCT Filed: Dec. 12, 2014

(86) PCT No.: PCT/IB2014/066833
§ 371 (c)(1),
(2) Date: Jul. 19, 2016

(87) PCT Pub. No.: WO2015/114423
PCT Pub. Date: Aug. 6, 2015

(65) Prior Publication Data
US 2016/0331341 A1 Nov. 17, 2016

Related U.S. Application Data

(60) Provisional application No. 61/932,922, filed on Jan. 29, 2014.

(51) Int. Cl.
*G06K 9/00* (2006.01)
*A61B 6/00* (2006.01)
(Continued)

(52) U.S. Cl.
CPC ............ *A61B 6/5264* (2013.01); *A61B 6/032* (2013.01); *A61B 6/4435* (2013.01); *A61B 6/463* (2013.01);
(Continued)

(58) Field of Classification Search
None
See application file for complete search history.

(56) References Cited

U.S. PATENT DOCUMENTS 7,277,565 B2 10/2007 Rasche
7,924,972 B2 4/2011 Kohler
(Continued)

OTHER PUBLICATIONS

Nett, et al., "Temporally Targeted Imaging Method Applied to ECG-Gated Computed Tomography", Academic Radiology, vol. 15., No. 1, Dec. 11, 2007.
(Continued)

*Primary Examiner* — Idowu O Osifade (57) ABSTRACT

A method includes obtaining projection data from a scan of a moving structure of interest. The method further includes reconstructing the projection data, generating first image data. The method further includes identifying a sub-set of the projection. The method further includes reconstructing the sub-set projection data, generating second image data. The method further includes identifying a region in which the moving structure of interest is located based on the first image data. The method further includes identifying a location of the moving structure of interest in the identified region based on the second image data.

20 Claims, 8 Drawing Sheets

(51) Int. Cl.
*A61B 6/03* (2006.01)
*G06T 11/00* (2006.01)
*G06T 7/215* (2017.01)

(52) U.S. Cl.
CPC .............. *A61B 6/503* (2013.01); *A61B 6/504* (2013.01); *A61B 6/5205* (2013.01); *A61B 6/5241* (2013.01); *G06T 7/215* (2017.01); *G06T 11/005* (2013.01); *G06T 11/008* (2013.01); *G06T 2207/10072* (2013.01); *G06T 2207/10081* (2013.01); *G06T 2207/10088* (2013.01); *G06T 2207/10104* (2013.01); *G06T 2207/10108* (2013.01); *G06T 2211/412* (2013.01)

(56) References Cited

U.S. PATENT DOCUMENTS

| | | | |
|---|---|---|---|
| 2008/0050001 | A1 | 2/2008 | Conwell |
| 2010/0074485 | A1* | 3/2010 | Movassaghi .......... A61B 6/504 382/128 |
| 2011/0044524 | A1* | 2/2011 | Wang .................... G01R 33/54 382/131 |
| 2011/0142313 | A1 | 6/2011 | Pack |
| 2011/0142315 | A1 | 6/2011 | Hsieh |
| 2013/0261439 | A1* | 10/2013 | Schmitt .................. A61B 6/032 600/424 |

OTHER PUBLICATIONS

Bundschuh, et al., "Local motion correction for lung tumours in PET/CT-first results", European Journal of Nuclear Medicine and Molecular Imaging, Springer, vol. 35, No. 11, Aug. 6, 2008.

Desjardins, et al., "ECG-Gated Cardiac CT", American Journal of Roentgenology, Apr. 2004, vol. 182 No. 4.

Isola, et al., "Motion compensated iterative reconstruction of a region of interest in cardiac cone-beam CT", Computerized Medical Imaging and Graphics 34 (2010) 149-159.

Isola, et al., "Cardiac motion-corrected iterative cone-beam CT reconstruction using a semi-automatic minimum cost path-based coronary centerline extraction", Computerized Medical Imaging and Graphics 36 (2012) 215-226.

* cited by examiner

SEGMENTATION OF MOVING STRUCTURE IN IMAGE DATA

CROSS REFERENCE TO RELATED APPLICATIONS

This application is the U.S. National Phase application under 35 U.S.C. § 371 of International Application No. PCT/IB 2014/066833, filed Dec. 12, 2014, published as WO 2015/114423 on Aug. 6, 2015, which claims the benefit of U.S Provisional Patent Application No. 61/932,922 filed Jan. 29, 2014. These applications are hereby incorporated by reference herein.

The following generally relates to imaging moving structure and more particular to segmenting moving structure in image data, and is described with particular application to computed tomography (CT). However, the following is also amenable to other imaging modalities such as positron emission tomography (PET), single photon emission tomography (SPECT), magnetic resonance (MR), x-ray tomography, and/or other modalities.

A computed tomography (CT) scanner generally includes an x-ray tube mounted on a rotatable gantry opposite a detector array across an examination region. The rotatable gantry and hence the x-ray tube rotate around the examination region and a subject therein. The x-ray tube emits radiation that traverses the examination region and the subject. The detector array detects radiation that traverses the examination region and generates projection data indicative thereof. A reconstructor reconstructs the projection data, generating volumetric image data indicative of the scanned subject.

However, subject motion during scanning may introduce artifact into the projection data and hence the reconstructed volumetric image data. For example, cardiac motion during a cardiac scan gated at a quiet phase of the cardiac cycle may result in blurring of the coronary vessels. Unfortunately, such motion artifact may make further processing of the coronary vessels, such as automatic and/or manual coronary artery segmentation, difficult, and segmentation of the coronary vessels from CT is used, for example, to facilitate the diagnosis of coronary lesions or, where the segmentation is performed in multiple different cardiac phases, for motion estimation and compensation.

Figure 1:
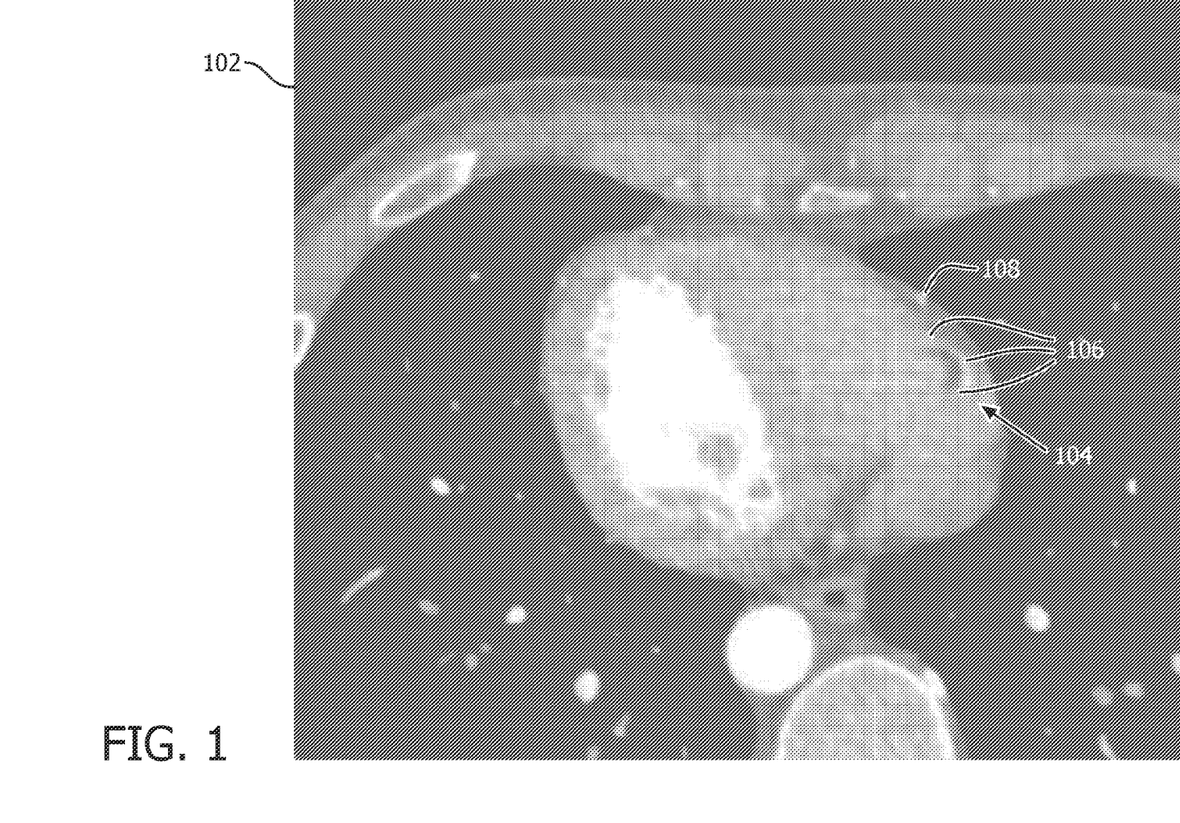
FIG. 1 shows image data from a contrast-enhanced cardiac axial scan in which a coronary vessel of interest is blurred due to cardiac motion.

FIG. 1 shows an example of such blurring. In FIG. 1, image data 102 from a contrast-enhanced cardiac axial scan is illustrated. A coronary artery 104 of interest moves, with the beating heart, during the scan. As a result, the coronary artery 104 shows up as a blurred arc 106 in the image data 102. The degree of blurring corresponds to the path of the motion and depends on the rotation speed of the rotating gantry and x-ray tube. With the vessel blurred as shown in FIG. 1, only a rough guess of the location of the vessel can be made. A vessel 108 represents a substantially less blurred vessel. In general, a non-burred vessel would show up a compact bright structure.

Aspects described herein address the above-referenced problems and others.

The following describes an approach to segment a moving structure from image data. With this approach, a first reconstruction provides lower temporal resolution of the moving structure of interest and surrounding structure. A second reconstruction, performed with a sub-set of the projection data used for the first reconstruction, has higher temporal resolution and thus less motion artifact than the first reconstruction. That is, the blurring in the second reconstruction is more compact because the project data for the second reconstruction covers a shorter time interval and hence there is less motion. The combination of the first and second reconstruction is used to segment the moving structure of interest.

In one aspect, a method includes obtaining projection data from a scan of a moving structure of interest. The method further includes reconstructing the projection data, generating first image data. The method further includes identifying a sub-set of the projection. The method further includes reconstructing the sub-set projection data, generating second image data. The method further includes identifying a region in which the moving structure of interest is located based on the first image data. The method further includes identifying a location of the moving structure of interest in the identified region based on the second image data.

In another aspect, a moving structure of interest segmentor includes a first reconstructor that reconstructs projection data corresponding to a scan of a moving structure, generating first image data. The moving structure of interest segmentor further includes a second reconstructor that reconstructs a sub-set of projection data, generating second image data. The moving structure of interest segmentor further includes a rendering engine that visually displays the first and the second image data. The moving structure of interest segmentor further includes an input device(s) that receives a first input indicative of a region in the first image data in which the moving structure of interest is located and a second indicative of a location within the region at which the moving structure of interest is located. The moving structure of interest segmentor further includes a segmentor that segments the moving structure of interest based on the location.

In another aspect, a computer readable storage medium is encoded with computer readable instructions. The computer readable instructions, when executed by a processor, causes the processor to: reconstruct at least two image data sets from different portions of a same set of projection data, wherein the at least two image data sets have different temporal resolution, locate moving structure of interest based on the at least two image data sets, and segment the moving structure of interest based on the located moving structure of interest.

The invention may take form in various components and arrangements of components, and in various steps and arrangements of steps. The drawings are only for purposes of illustrating the preferred embodiments and are not to be construed as limiting the invention.

Figure 2:
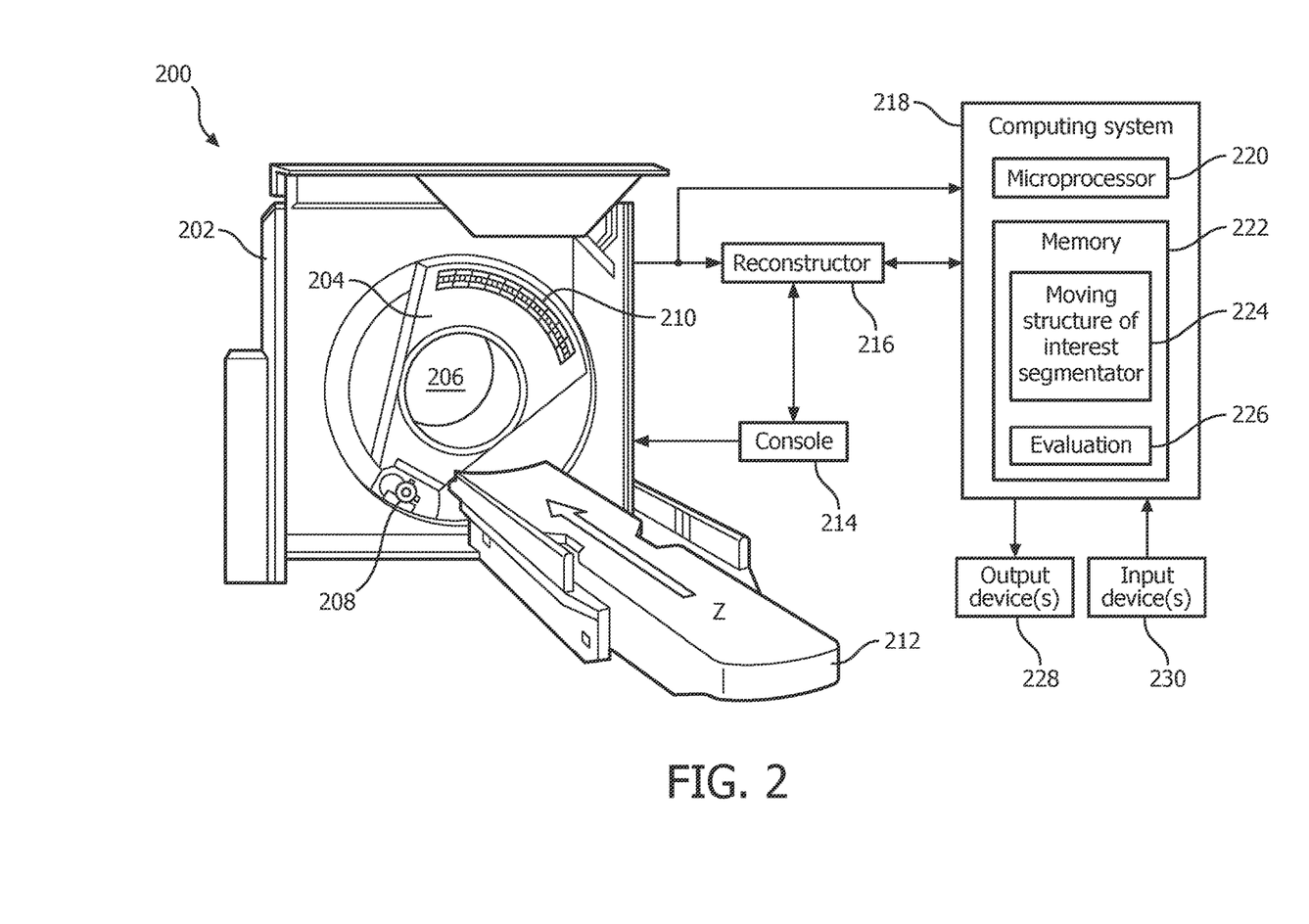
FIG. 2 schematically illustrates an example computing system with a moving structure of interest segmentor in connection with an imaging system.

Initially referring to FIG. 2, an example imaging system 200, such as a computed tomography (CT) scanner, is schematically illustrated. The imaging system 200 includes a generally stationary gantry 202 and a rotating gantry 204. The rotating gantry 204 is rotatably supported by the stationary gantry 202 and rotates around an examination region 206 about a longitudinal or z-axis.

A radiation source 208, such as an x-ray tube, is rotatably supported by the rotating gantry 204. The radiation source 208 rotates with the rotating gantry 204 and emits radiation that traverses the examination region 206.

A one or two-dimensional radiation sensitive detector array 210 subtends an angular arc opposite the radiation source 208 across the examination region 206. The detector array 210 includes a plurality of rows of detectors that extend along the z-axis direction. The detector array 210 detects radiation traversing the examination region 206 and generates projection data indicative thereof.

A subject support 212, such as a couch, supports an object or subject in the examination region 206. The support can be before, during and/or after scanning. This includes loading and unloading the subject in the examination region 206.

A computing system serves as an operator console 214 and includes a human readable output device such as a monitor and an input device such as a keyboard, mouse, etc. The console 214 allows an operator to interact with the scanner 200 via a graphical user interface (GUI) and/or otherwise. For instance, the user can select a 180 degree cardiac scan protocol (e.g., in which data is acquired over 180 degrees and includes data corresponding to 180 degrees plus a source fan). The user can also select a scan that is less than 180 degrees and a scan that is greater than 180 degrees.

A reconstructor 216 reconstructs the projection data and generates volumetric data indicative thereof. This includes utilizing a reconstruction algorithm based on the acquisition protocol. For example, a 180 degree reconstruction can be utilized for scans performed with 180 degree acquisition protocol or a protocol with a higher angular range.

A computing system 218 includes at least one microprocessor 220 and a computer readable storage medium ("memory") 222. The memory 222 excludes transitory medium and includes physical memory and/or other non-transitory storage medium. The microprocessor 220 executes at least a moving structure of interest segmentor 224 instruction(s) stored in the memory 222. The microprocessor 220 may also executes a computer readable instruction carried by a carrier wave, a signal or other transitory medium. The computing system 218 can be part of the console 214 and/or separate therefrom (as illustrated in FIG. 2).

The moving structure of interest segmentor 224 instruction(s) at least includes an instruction(s) for processing at least projection and/or image data of a scanned moving structure of interest. As described in greater detail below, this includes generating at least two sets of image data from the projection data, including a first set of image data with first temporal resolution and first motion artifact and a second set of image data with second temporal resolution and second motion artifact, where the first temporal resolution is lower and the first motion artifacts are greater than the second temporal resolution and the second artifacts respectively, and utilizing one or more of the at least two sets of image data to segment the scanned moving structure of interest.

This approach provides separate sets of image data from a single scan, one that can be used as a guide to a general region in the image data where the scanned moving structure of interest is located (the lower temporal resolution image data) and one to identify the scanned moving structure of interest in the general region (the lower motion artifact image data). The separate sets of image data can be viewed individually or in combination, for example, as separate or combined image data sets. This approach may mitigate guessing a location of the scanned moving structure of interest at a particular time point of interest, for example, due to blurring of the scanned moving structure of interest in the image data, in a configuration in which only a single set of image data is utilized.

In the illustrated embodiment, the memory 222 also includes an evaluation 226 instruction. The evaluation 226 instruction, in one instance, performs a quantitative evaluation of the moving structure of interest based on the segmented moving structure of interest. The evaluation 226 instruction, in another instance, utilizes the segmented moving structure of interest in connection with motion estimation and compensation. In other instances, the evaluation 226 instruction utilizes the segmented moving structure of interest for other processing.

The computing system 218 further includes an output device(s) 228 such as a display monitor, a filmer, etc., and an input device(s) 230 such as a mouse, keyboard, etc. The output device(s) 228 can be used to visually display image data such as image data reconstructed at a motion phase of interest and/or at one or more other motion phases. The input device(s) 230, as described in greater detail below, can be used to one or more of select an angular range for a scan reconstruction, combine image data sets, toggle between image data sets, segment tissue of interest, etc.

Figure 3:
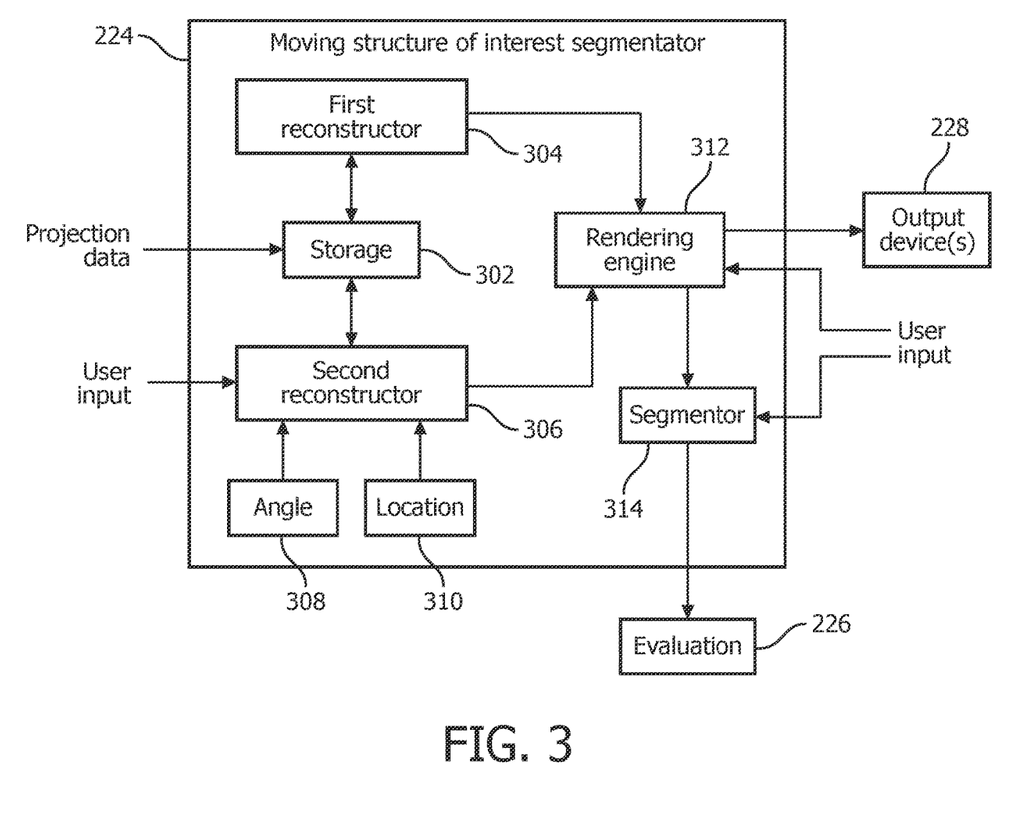
FIG. 3 schematically illustrates an example of the moving structure of interest segmentor.

FIG. 3 schematically illustrates an example of moving structure of interest segmentor 224.

The moving structure of interest segmentor 224 includes storage 302, which stores projection data. The projection data can be from and/or generated by the imaging system 200 and/or other imaging system. Alternatively, the projection data can be from a data repository such as a picture archiving and communication system (PACS), a radiology information system (RIS), a hospital information system (HIS), etc. In a variation, the storage 302 is omitted and the projection data is provided to another component of the moving structure of interest segmentor 224.

The moving structure of interest segmentor 224 includes a first reconstructor 304. The first reconstructor 304 reconstructs the full set of projection data, producing first image data. The full set of projection data may correspond to a 180 degree scan (i.e., 180 degrees plus a source fan) or other scan, including a scan that covers less than 180 degrees and a scan that covers more than 180 degrees. The resulting image data provides lower temporal resolution for the acquired projection data, relative to a reconstruction that uses only a sub-portion of the full set of projection data.

The moving structure of interest segmentor 224 further includes a rendering engine 312. The rendering engine 312, in the illustrated embodiment, visually displays in human readable format the first image data via a display of the output device(s) 228 and/or other display. The image data 102 of FIG. 1 illustrates an example of a reconstruction of a full set of projection data corresponding to a 180 degree scan. In this example, the anatomical features are distinguishable since a 180 degree scan provides a complete set of projections.

The moving structure of interest segmentor 224 further includes a second reconstructor (partial scan) 306. The second reconstructor 306 reconstructs only a sub-portion of the full set of projection data, producing second image data. An angle setting 308 and a location setting 310 identify the sub-portion. For example, where the projection data corresponds to a 180 degree scan, the angle setting 308 identifies an angle of less than 180 degrees (e.g., 160 degrees, 90 degrees, 30 degrees, etc.) and the location setting 310 identifies a point in time of the 180 degrees scan at which the angle of the angle setting 308 is centered about.

Figure 4:
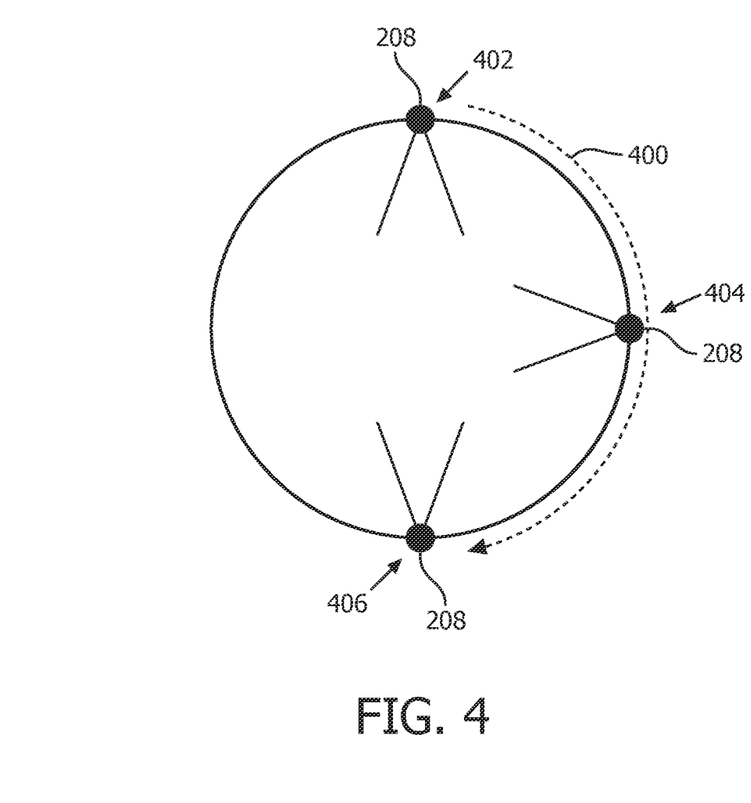
FIG. 4 schematically illustrates a 180 degree scan.
Figure 5:
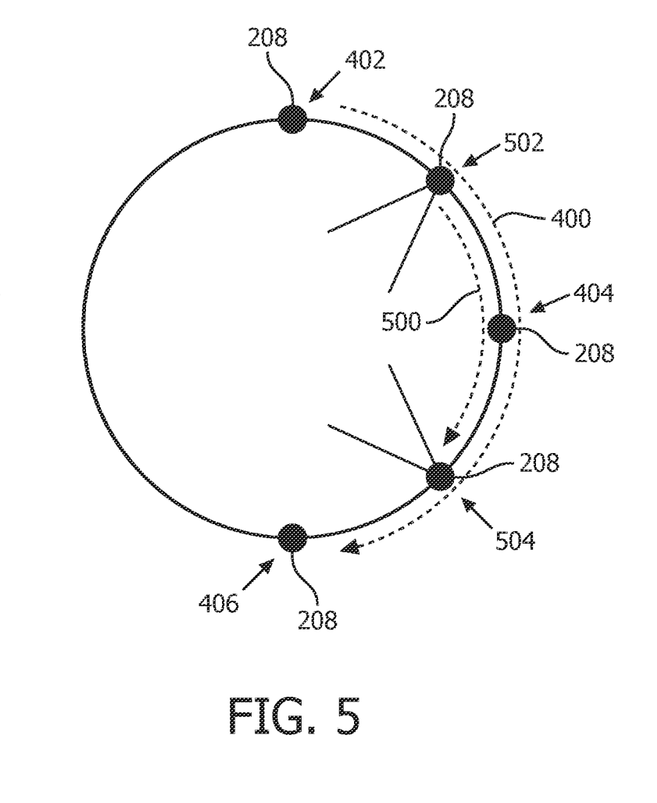
FIG. 5 schematically illustrates an angular subset of the 180 degree scan of FIG. 4, centered on the 180 degree scan, identified for a lower motion artifact reconstruction.

By way of non-limiting example, in one instance, the angle setting 308 is 90 degrees and the location setting 310 is the central time point of the 180 degree scan. FIGS. 4 and 5 graphically illustrate this. FIG. 4 shows an example 180 degree scan 400 with the radiation source 208 that traverses from a 12 O'clock position 402 through a central point in time at a 3 O'clock position 404 to a 6 O'clock position 406. FIG. 5 shows an angular range 500 of 90 degrees, from 502 to 504, centered about the central point in time of the 180 degree scan at the 3 O'clock position 404.

Returning to FIG. 3, the angle setting 308 and/or the location setting 310 can be a default, a user preference, a protocol based, etc. setting. Alternatively, the angle setting 308 and/or the location setting 310 is identified by a user input from a user, for example, via the input device(s) 230. Generally, the angle setting 308 is less than the angular range of the full scan. As a result, the second image data, relative of the first image data, will have less motion artifact. Furthermore, since the time interval of the sub-portion is less than the time interval of the full set of projection data, the second image data will have higher temporal resolution, relative of the first image data.

Figure 6:
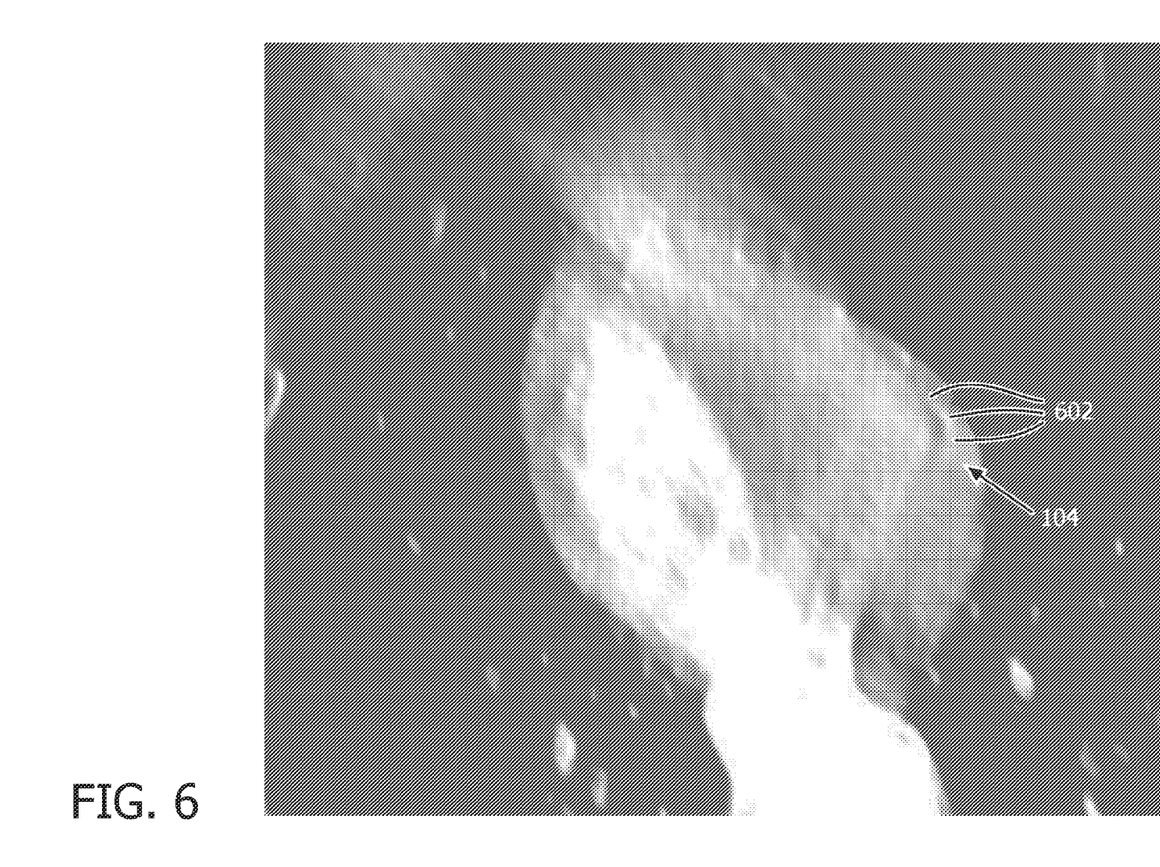
FIG. 6 shows lower motion artifact image data corresponding to the lower motion artifact reconstruction of FIG. 5.

The lower motion artifact and the higher temporal resolution are shown in FIG. 6. FIG. 6 shows the same coronary artery 104 shown in FIG. 1. However, in FIG. 6, the same coronary artery 104 is a smaller blurred arc 602 (more compact) relative to the blurred arc 106 in FIG. 1. Since less than 180 degrees of data is acquired, the set of projections does not fill the 2D Fourier space, which leads to reconstruction errors. This is shown in FIG. 6 through the highly distorted anatomical structure, relative to the anatomical structure of FIG. 1.

Returning to FIG. 3, the rendering engine 312 visually displays in human readable format the second image data via a display of the output device(s) 228 and/or other display. In one instance, the first image data and the second image data are concurrently visually presented, for example, next to each other. This is shown in connection with FIG. 7. In another instance, only one of the first image data or the second image data is visually presented at any given time. The user, via the input device(s) 230, can toggle back and forth between the first image data and the second image data. The user uses the first image data to identify a region of moving structure of interest and the second image data to locate the moving structure of interest in the region.

Figure 7:
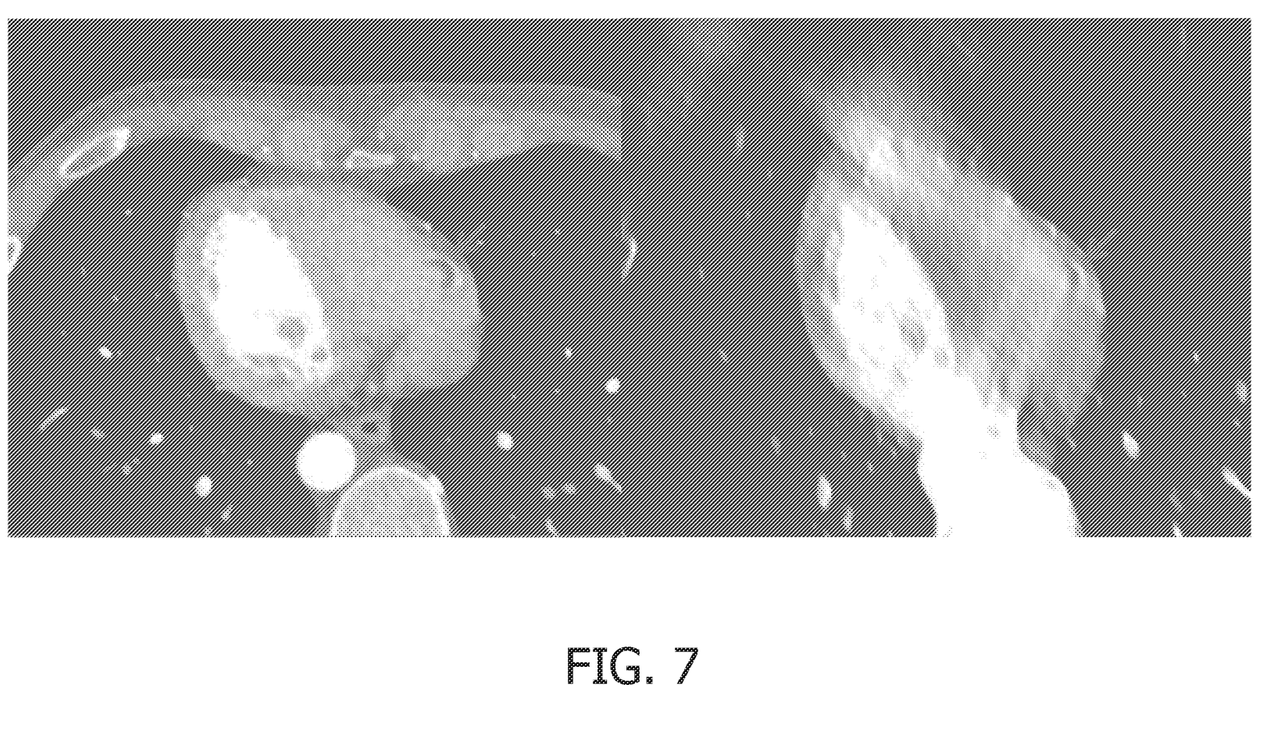
FIG. 7 shows an example visualization in which lower temporal resolution and lower motion artifact image data are concurrently displayed.

In yet another instance, the first image data and the second image data are fused or overlaid. In this instance, one or both of the first image data and the second image data can have a transparency and/or opacity setting. The user can adjust the transparency and/or opacity setting to visually emphasize or de-emphasize the first image data and/or the second image data, including a user desired blend of both the first and the second image data. Again, the user uses the first image data to identify a region of moving structure of interest and the second image data to locate the moving structure of interest in the region.

Returning to FIG. 3, the moving structure of interest segmentor 224 further includes a segmentor 314. The segmentor 314 allows a user to segment the moving structure of interest. For this, the segmentor 314 receives a signal indicative of a region to segment selected by the user. The region can be manually identified by the user (e.g., through free hand drawings, etc.) and/or automated segmentation software tools. In the latter case, the user can accept, modify and/or reject the segmentation. The user, via the input device(s) 230, can pan, zoom, rotate, and/or other manipulate the rendered image data to facilitate segmentation.

The segmented moving structure of interest can be identified in one of the first or second image data and automatically placed in the other of the first or second image data as the first or second image data are inherently registered and share the same coordinate system. The segmented moving structure of interest can be propagated through a volume of axial images using the approach described above for each axial slice. In another instance, the above described approach is applied every other slice, every fifth slice, etc., with interpolation or other approach used to construct the segmentation there between.

In the illustrated embodiment, the segmented moving structure of interest is evaluated by the evaluation 226 instruction(s). For example, in one instance, the moving structure of interest includes at least one centerline of at least one coronary vessel, and the evaluation 226 instruction(s) evaluates the segmented moving structure of interest in connection with a quantitative evaluation of coronary disease. In another instance, for example, where the centerline is determined in different cardiac phases, the evaluation 226 instruction(s) evaluates the segmented moving structure of interest in connection with motion estimation and compensation.

In FIG. 3, the first reconstructor 304 and the second reconstructor 306 are shown as two separate reconstructors. In a variation, the first reconstructor 304 and the second reconstructor 306 can be implemented with or are sub-reconstructors of the same reconstructor. Furthermore, one or more of the first reconstructor 304 and the second reconstructor 306 can be implemented via the reconstructor 216 (FIG. 2).

Figure 8:
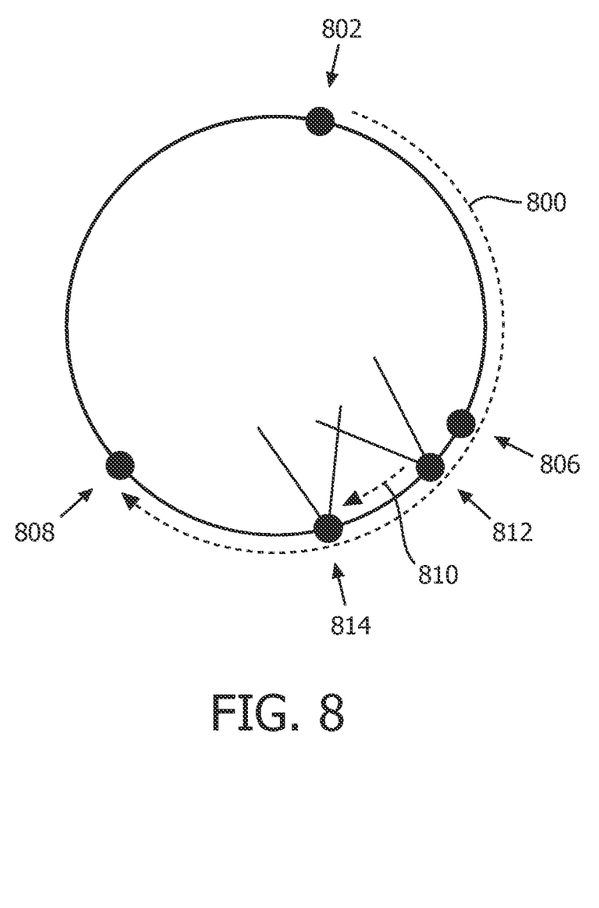
FIG. 8 schematically illustrates a less than 90 degree angular subset of a greater than 180 degree scan, not centered on the scan.

FIG. 8 shows a variation of FIGS. 4 and 5 in which a full scan 800 is greater than 180 degrees, and a sub-portion 810 is less than 90 degrees and is not centered on the full scan. In this example, the full scan starts at 802, passes a central location 806, and ends at 808. The sub-portion 810 covers a sub-range from 812 to 814 and is not centered at 806. The particular center point and angular range may correspond to the particular motion phase of interest, a tradeoff between temporal resolution and motion artifact, etc.

Although the above is described in connection with axial scans, it is to be understood that the above also applies to helical scans.

Figure 9:
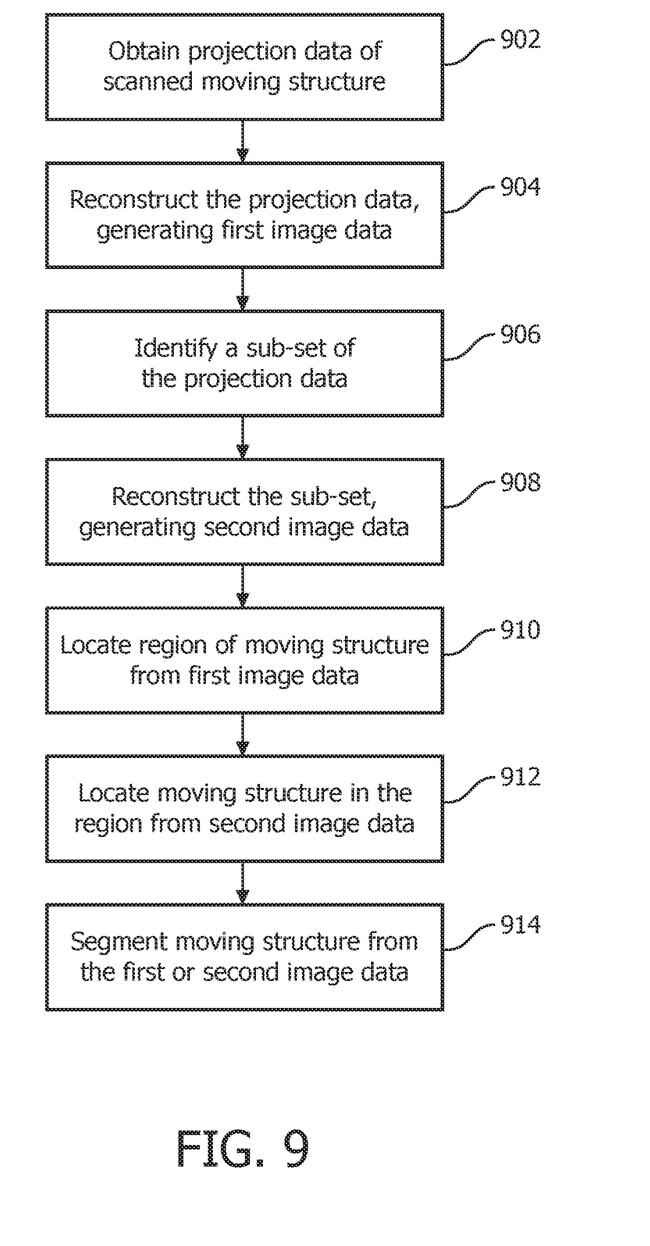
FIG. 9 illustrates a method for segmenting a moving structure of interest in image data.

FIG. 9 illustrates an example method in accordance with embodiments disclosed herein.

It is to be appreciated that the ordering of the acts in the methods is not limiting. As such, other orderings are contemplated herein. In addition, one or more acts may be omitted and/or one or more additional acts may be included.

At 902, projection data from a scan of a moving subject is obtained.

At 904, the projection data is reconstructed, generating first image data.

At 906, a sub-set of the project data is identified for a second reconstruction.

At 908, the sub-set of the projection data is reconstructed, generating second image data.

At 910, the first image data is utilized to locate a region in which a moving structure of interest is located.

At 912, the second image data is utilized to locate the moving structure of interest within the region.

At 914, the moving structure of interest is segmented from one of the first or second image data.

The segmented moving structure of interest can be further evaluated, as described herein.

The above methods may be implemented by way of computer readable instructions, encoded or embedded on computer readable storage medium, which, when executed by a computer processor(s), cause the processor(s) to carry out the described acts. Additionally or alternatively, at least one of the computer readable instructions is carried by a signal, carrier wave or other transitory medium.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

The invention claimed is:

1. A method, comprising:
    obtaining projection data from a scan of a moving structure of interest;
    reconstructing the projection data, generating first image data;
    identifying a sub-set of the projection data;
    reconstructing the sub-set of the projection data, generating second image data;
    identifying a region in the first image data in which the moving structure of interest is located; and
    identifying a location of the moving structure of interest in the second image data based on the identified region in the first image data.

2. The method of claim 1, wherein the first image data has a first temporal resolution and the second image data has a second temporal resolution, wherein the first temporal resolution is lower than the second temporal resolution.

3. The method of claim 1, wherein the first image data has a first level of motion artifact and the level of motion artifact, wherein the first level of motion artifact is greater than the second level of motion artifact.

4. The method of any of claim 1, comprising:
    visually displaying, concurrently, the first image data and the second image data;
    receiving an input signal indicating the location of the moving structure of interest in the second image data; and
    automatically identifying the location of the moving structure of interest in the first image data based on the input signal.

5. The method of claim 1, comprising:
    visually displaying only one of the first image data or the second image data;
    receiving an input signal; and
    switching between visual display of the first image data and the second image based on the input signal.

6. The method of claim 1, comprising:
    visually displaying the first image data and the second image data superimposed over each other;
    receiving an input signal indicative of at least one of an opacity or transparency level for at least one of the first image data and the second image data; and
    visually displaying the first image data and the second image data based on the input signal.

7. The method of claim 1, wherein the first image data corresponds to a 180 degree scan in which data is acquired for 180 degrees plus a source fan.

8. The method of claim 1, wherein the first image data corresponds to a scan greater than 180 degree.

9. The method of claim 7, wherein the second image data corresponds to less than the 180 degree scan.

10. The method of claim 9, wherein the sub-set of projection data is centered at a central time point of the projection data.

11. The method of claim 1, wherein the first image data includes a plurality of individual axial slices, and further comprising:
    propagating the identified location through the plurality of individual axial slices.

12. The method of claim 1, further comprising:
    segmenting the moving structure of interest, producing segmented moving structure of interest.

13. The method of claim 12, further comprising:
    performing a quantitative evaluation on the segmented moving structure of interest.

14. The method of claim 12, further comprising:
    motion compensating at least one of the projection data or the first image data based on the segmented moving structure of interest.

15. A system, comprising:
    a processor, including:
        a first reconstructor that reconstructs projection data corresponding to a scan of a moving structure, generating first image data;
        a second reconstructor that reconstructs a sub-set of projection data, generating second image data;
        a rendering engine that visually displays the first and the second image data;
        an input that receives a first input indicative of a region in the first image data in which the moving structure of interest is located and a second input indicative of a location within the region and in the second image data at which the moving structure of interest is located; and
        a segmentor that segments the moving structure of interest based on the location of the moving structure of interest.

16. The system of claim 15, where the projection data corresponds to an angular range, and the processor identifies a sub-portion of the angular range for the sub-set of projection data.

17. The system of claim 16, wherein the processor identifies a time point of the projection at which the sub-portion is centered.

18. The system of claim 15, further comprising:
    a display, wherein the first image data and the second image data are concurrently visually displayed via the display,
    wherein the input receives an input signal indicating the location of the moving structure of interest in the second image data, and the rendering engine automatically determines the location of the moving structure of interest in the first image data based on the input signal.

19. The system of claim 15, further comprising:
a display, wherein the first image data and the second image data are alternately visually displayed or simultaneously displayed superimposed.

20. A computer readable storage medium encoded with one or more computer executable instructions, which, when executed by a processor of a computing system, causes the processor to:
reconstruct at least two image data sets from different portions of a same set of projection data, wherein the at least two image data sets have different temporal resolution;
locate moving structure of interest based on the at least two image data sets by:
identifying a region in a first image data set of the at least two image data sets in which the moving structure of interest is located; and
locating the moving structure of interest in a second image data set of the at least two image data sets based on the identified region in the first image data set; and
segment the moving structure of interest based on the located moving structure of interest.

\* \* \* \* \*